United States Patent
Clerc et al.

(10) Patent No.: US 10,426,641 B2
(45) Date of Patent: Oct. 1, 2019

(54) STENT WITH ANTI-MIGRATION FEATURE

(71) Applicant: BOSTON SCIENTIFIC SCIMED, INC., Maple Grove, MN (US)

(72) Inventors: Claude O. Clerc, Marlborough, MA (US); Sri Tupil, Acton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 15/206,577

(22) Filed: Jul. 11, 2016

(65) Prior Publication Data
US 2016/0317330 A1  Nov. 3, 2016

Related U.S. Application Data

(63) Continuation of application No. 12/354,392, filed on Jan. 15, 2009, now Pat. No. 9,439,790.
(Continued)

(51) Int. Cl.
*A61F 2/82* (2013.01)
*A61F 2/848* (2013.01)
*A61F 2/07* (2013.01)
*A61F 2/90* (2013.01)
*A61L 31/10* (2006.01)
(Continued)

(52) U.S. Cl.
CPC ............ *A61F 2/848* (2013.01); *A61F 2/07* (2013.01); *A61F 2/90* (2013.01); *A61L 31/10* (2013.01); *A61L 31/125* (2013.01); *A61L 31/14* (2013.01); *A61F 2002/072* (2013.01); *A61F 2002/075* (2013.01); *A61F 2002/30322* (2013.01); *A61F 2002/8486* (2013.01); *A61F 2220/0016* (2013.01); *A61F 2230/005* (2013.01); *A61F 2230/0078* (2013.01); *A61F 2250/0026* (2013.01); *A61F 2250/0037* (2013.01); *A61F 2250/0039* (2013.01)

(58) Field of Classification Search
CPC .............. A61F 2/90; A61F 2002/072; A61F 2002/075; A61F 2002/30322; A61F 2002/8486; A61F 2220/0016; A61F 2230/005; A61F 2230/0078; A61F 2250/0026; A61F 2250/0037; A61F 2250/0039; A61F 2/07; A61F 2/848; A61F 2002/3011; A61F 2002/8483; A61F 2/82; A61L 31/10; A61L 31/125; A61L 31/14

See application file for complete search history.

(56) References Cited

U.S. PATENT DOCUMENTS 4,798,606 A  1/1989  Pinchuk
5,116,360 A  5/1992  Pinchuk et al.
(Continued)

FOREIGN PATENT DOCUMENTS

WO   9721401 A1     6/1997
WO   2004002370 A1  1/2004
WO   2008157362 A2  12/2008

*Primary Examiner* — Seema Mathew
(74) *Attorney, Agent, or Firm* — Seager, Tufte & Wickhem, LLP

(57) ABSTRACT

An intraluminal prosthesis includes an outer three-dimensional (3D) anti-migration structure that is attached to the outer wall of a fully covered or partially covered stent to prevent migration and still allow stent removal at a later period of time. A method of manufacturing the intraluminal prosthesis includes attaching the anti-migration structure by usage of a polymer such as polyurethane.

17 Claims, 9 Drawing Sheets

Related U.S. Application Data

(60) Provisional application No. 61/021,764, filed on Jan. 17, 2008.

(51) Int. Cl.
*A61L 31/12* (2006.01)
*A61L 31/14* (2006.01)
*A61F 2/30* (2006.01)

(56) References Cited

U.S. PATENT DOCUMENTS

| | | | |
|---|---|---|---|
| 5,330,500 A * | 7/1994 | Song | A61F 2/90 606/198 |
| 5,556,426 A | 9/1996 | Popadiuk et al. | |
| 6,056,993 A | 5/2000 | Leidner et al. | |
| 6,110,198 A | 8/2000 | Fogarty et al. | |
| 6,162,244 A | 12/2000 | Braun et al. | |
| 6,273,917 B1 * | 8/2001 | Inoue | A61F 2/07 623/1.15 |
| 6,447,835 B1 | 9/2002 | Wang et al. | |
| 6,626,936 B2 | 9/2003 | Stinson | |
| 6,890,348 B2 | 5/2005 | Sydney et al. | |
| 10,195,066 B2 * | 2/2019 | Behan | A61F 2/04 |
| 2002/0052644 A1 | 5/2002 | Shaolian et al. | |
| 2002/0099441 A1 * | 7/2002 | Dehdashtian | A61F 2/07 623/1.51 |
| 2002/0165601 A1 * | 11/2002 | Clerc | A61F 2/07 623/1.13 |
| 2002/0169498 A1 | 11/2002 | Kim et al. | |
| 2003/0204235 A1 | 10/2003 | Edens et al. | |
| 2004/0019375 A1 * | 1/2004 | Casey, II | A61F 2/06 623/1.28 |
| 2004/0034403 A1 | 2/2004 | Schmitt | |
| 2004/0034407 A1 | 2/2004 | Sherry | |
| 2004/0106904 A1 * | 6/2004 | Gonnelli | A61B 17/205 604/173 |
| 2005/0080478 A1 * | 4/2005 | Barongan | A61B 17/320725 623/1.14 |
| 2005/0273121 A1 * | 12/2005 | Sato | A61B 17/11 606/153 |
| 2006/0147612 A1 | 7/2006 | Da Rocha Loures | |
| 2006/0149349 A1 * | 7/2006 | Garbe | A61B 17/11 623/1.11 |
| 2006/0200226 A1 * | 9/2006 | Furst | B22F 3/16 623/1.15 |
| 2007/0055365 A1 * | 3/2007 | Greenberg | A61F 2/01 623/1.44 |
| 2007/0123969 A1 | 5/2007 | Gianotti | |
| 2007/0179590 A1 * | 8/2007 | Lu | A61F 2/07 623/1.16 |
| 2008/0319540 A1 | 12/2008 | Jordan et al. | |
| 2009/0192518 A1 * | 7/2009 | Golden | A61F 2/95 606/108 |
| 2011/0172760 A1 * | 7/2011 | Anderson | A61B 17/0057 623/1.15 |
| 2012/0041412 A1 * | 2/2012 | Roth | A61M 25/10 604/500 |
| 2013/0158673 A1 * | 6/2013 | Toomey | A61F 2/04 623/23.7 |
| 2013/0172983 A1 | 7/2013 | Clerc et al. | |
| 2013/0184808 A1 | 7/2013 | Hall et al. | |
| 2013/0231753 A1 * | 9/2013 | Liddy | A61L 31/10 623/23.7 |
| 2013/0268063 A1 * | 10/2013 | Firstenberg | A61F 2/06 623/1.46 |
| 2014/0099279 A1 * | 4/2014 | Furst | A61K 31/436 424/85.1 |
| 2014/0148897 A1 * | 5/2014 | Matheny | A61L 27/58 623/1.36 |
| 2014/0277395 A1 * | 9/2014 | Firstenberg | A61F 2/07 623/1.36 |
| 2014/0277442 A1 * | 9/2014 | Seddon | A61F 2/848 623/9 |
| 2014/0277562 A1 | 9/2014 | Seddon et al. | |
| 2014/0330305 A1 * | 11/2014 | Rood | A61F 2/01 606/200 |
| 2015/0045881 A1 * | 2/2015 | Lim | A61F 2/2418 623/2.38 |
| 2015/0051693 A1 * | 2/2015 | Bertolino | B29C 66/52272 623/1.13 |
| 2015/0051708 A1 * | 2/2015 | Anderson | A61B 17/064 623/23.7 |
| 2015/0073529 A1 | 3/2015 | Fleury et al. | |
| 2015/0282955 A1 * | 10/2015 | Guler | A61F 2/86 623/1.44 |
| 2015/0342760 A1 * | 12/2015 | Christakis | A61F 2/90 623/1.2 |
| 2016/0095724 A1 * | 4/2016 | Harris | A61F 2/07 623/23.7 |
| 2016/0106559 A1 | 4/2016 | Shin et al. | |
| 2016/0128852 A1 * | 5/2016 | Leanna | A61F 2/89 623/9 |
| 2016/0158040 A1 * | 6/2016 | Zupkofska | A61F 2/82 623/23.7 |
| 2016/0228268 A1 * | 8/2016 | Hingston | A61F 2/848 |
| 2017/0014247 A1 * | 1/2017 | Ryan | A61F 2/88 |
| 2017/0100266 A1 * | 4/2017 | Fulkerson | A61F 2/848 |
| 2017/0319390 A1 * | 11/2017 | Skovlund | A61K 9/0046 |
| 2018/0092732 A1 * | 4/2018 | Kringle | A61F 2/848 |

* cited by examiner

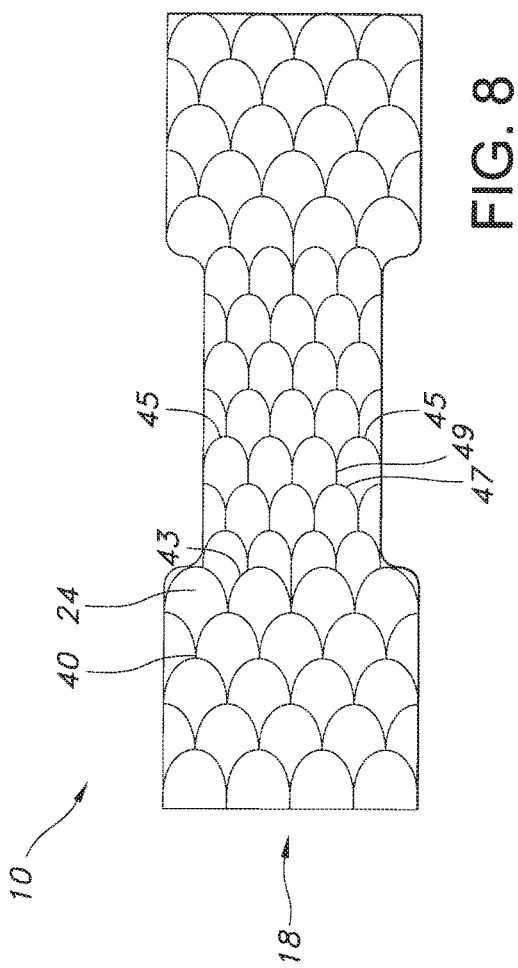
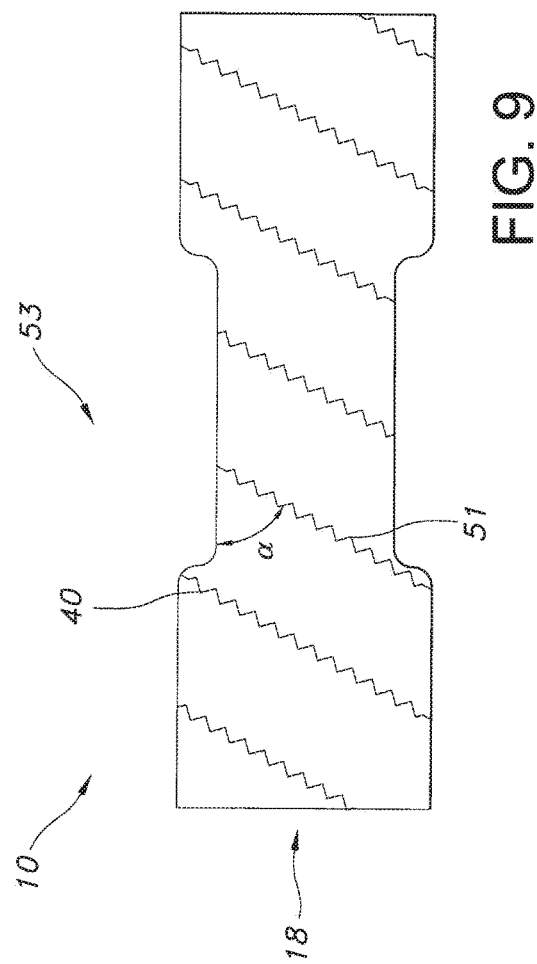

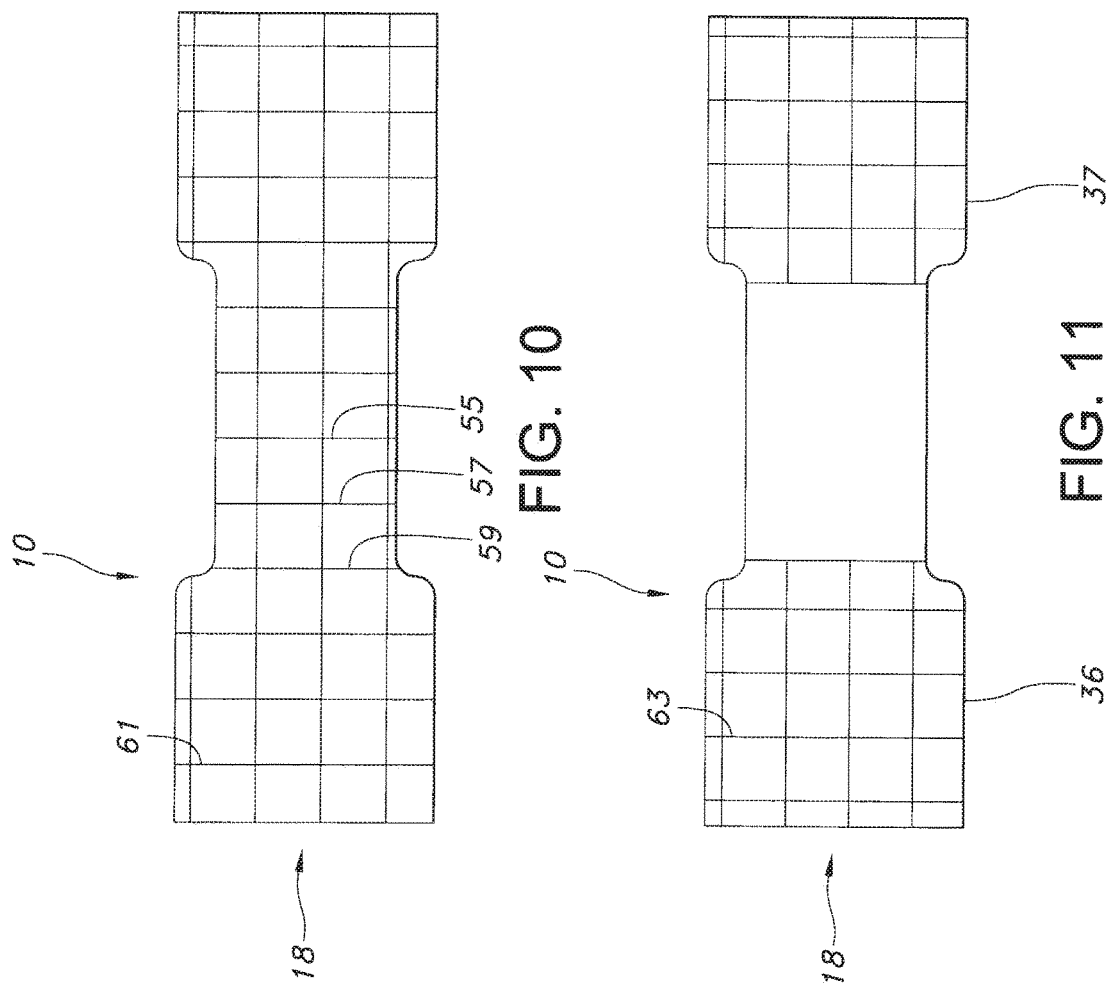

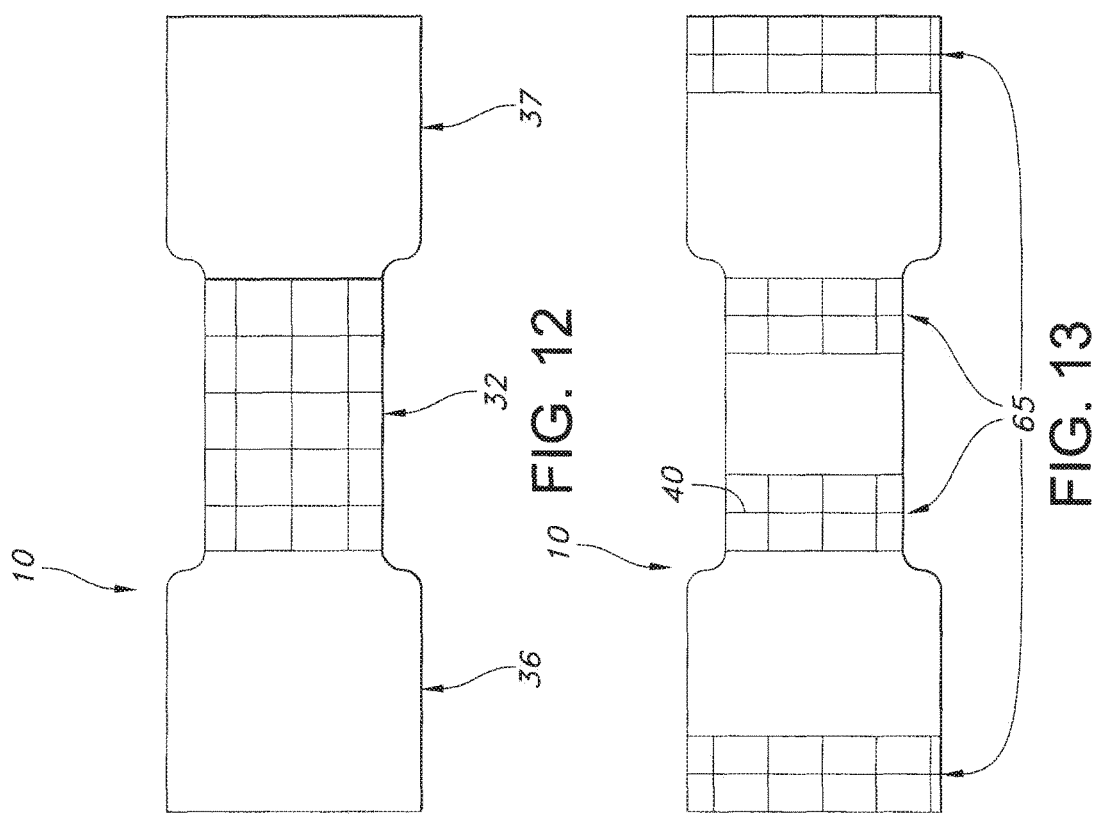

STENT WITH ANTI-MIGRATION FEATURE

CROSS-REFERENCE TO RELATED APPLICATIONS

This application is a continuation of U.S. application Ser. No. 12/354,392, filed Jan. 15, 2009 which claims priority to U.S. Provisional Application No. 61/021,764, filed Jan. 17, 2008, the entire contents of which are incorporated herein by reference.

FIELD OF THE INVENTION

The present invention relates to an intraluminal prosthesis having an anti-migration feature. More particularly, the present invention relates to a stent with a three-dimensional (3D) anti-migration exterior portion designed to prevent migration of the stent once deployed, as well as resist and/or prevent ingrowth on the stent itself to facilitate its removal at a later time.

BACKGROUND OF THE INVENTION

Stents, in general, may be categorized as permanent, removable, or bioresorbable. Permanent stents are retained in place and incorporated into the lumen wall of a body by promoting ingrowth. Removable stents are removed from the body lumen when the stent is no longer desired. A bioresorbable stent may be composed of, or include, biodegradable material or bioresorbable material which may be broken down by the body and absorbed or passed from the body when it is no longer needed. In treating many bodily vessels, removable stents may be preferred over a permanent stent. For example, many esophageal stenoses procedures require stent removal at a specified date. Further, because it is difficult to predict the exact biodegrading time table of a bioresorbable stent, esophageal technology for instance, in general, has focused on the removable stent prosthesis.

A graft is another type of endoluminal prosthesis which is used to repair and replace body lumina. It is also known to combine a stent and a graft to form a composite stent device. Such composite stent device may provide additional support for weakened sections of a lumen.

The benefits and disadvantages of composite stent devices may be dependent on the extent of the coverings. For instance, bare stents can allow tissue ingrowth in the openings between the struts and therefore may have a low migration rate (undesired longitudinal movement within luminal surfaces). However, bare stents may be very difficult to remove after they have been implanted for a few weeks. In some cases, the ingrowth in the opening between the struts can continue to grow until the patency of the lumen structure is totally obstructed.

Partially covered stents were developed as a means to prevent or slow tissue ingrowth within portions of the body of the stent. However, these configurations also do not totally prevent tissue ingrowth. The tissue ingrowth may occur into openings of cells in the stent wall at the uncovered portions, making the stent still difficult to remove and prone to occlusion by tissue ingrowth.

Fully covered stents are designed to prevent tissue ingrowth along the entire length of the stent and are therefore should be much easier to remove than bare or partially covered stents even after having been implanted for an extended period of time. Covered stents may also slow the growth of tumors and fistula. However, because the covered stents generally do not include any friction inducing structure, their migration rate along the body lumens is higher than the migration rate of bare or partially covered stents. Thus, there is a need for a stent that resists migration and can be easily removed after a given time period.

SUMMARY OF THE INVENTION

The present invention is directed to intraluminal prostheses such as a fully or partially covered stent that may be repositionable and/or removable. The intraluminal prosthesis may also be resistant to movement or migration within a body lumen once deployed. The outside wall of a fully (or partially) covered stent may be integrally preformed with a three-dimensional (3D) anti-migration structure. Alternatively, the stent may be embedded within or have attached to its surface, a thin anti-migration structure comprising one or more filaments or individual three-dimensional structures. The anti-migration structure may function to lessen stent migration by roughening the outside surface of the stent, which is in contact with the inner surface of the body lumen into which it is placed. Simultaneously, the stent body may prevent or minimize the tissue ingrowth adjacent thereto. The external anti-migration structure may be formed desirably very thin and may optionally be arranged in a pattern which provides for low profile delivery device.

A method of manufacturing a prosthesis is also disclosed. The method may include continuous fiber winding, where a solution or dispersion is extruded through a small orifice to form or place a polymeric fiber on the surface of the stent. A particular structure pattern may be obtained by continuously winding the fiber onto a rotating mandrel. For instance, the pattern of a stent may be formed on the mandrel or a hollowing covering may be created to be attached to a stent. Other methods of manufacturing the prosthesis described herein are contemplated.

In another embodiment, there is provided a method of forming a prosthesis, which includes providing a stent, and attaching a covering to the stent, the covering including an anti-migration structure which may provide anti-slip or anti-migration properties to the prosthesis. The covering is preferably a biocompatible material, for instance, a polymer which may be attached to the stent in various ways, including but not limited to being placed over the stent and adhered to the stent with use of a heat-shrink tube and heat. Other adhesion methods include placing the anti-migration structure on a stent, and spraying the stent and the anti-migration structure with a binder such as a polyurethane polymer.

Additionally, in accordance with the present invention, intraluminal prosthesis may include a radially self-expanding or a balloon expanding stent. The stent body may include a barrier region circumscribed by a film such as silicone to reduce tumor or ingrowth. Further, the barrier region may be combined with a fixation region of open weave construction. The stent may be resistant to migration and to tumor ingrowth, and may be configured to allow inner body lumen recovery gradually along its length after deployment.

Other objects and features of the invention will be evident from the following detailed description of the embodiments and practices included in the invention and from the drawings herewith.

BRIEF DESCRIPTION OF THE DRAWINGS

FIG. 8 illustrates a side plan view of another embodiment of the present invention showing a knitted graft configuration;

FIG. 9 illustrates a plan view of further another embodiment of the present invention showing a spiral graft configuration;

FIG. 10 illustrates a plan view of yet another embodiment of the present invention showing a "checker-board" graft configuration;

FIG. 11 illustrates a plan view of yet another embodiment of the present invention, showing the graft on the flares only;

FIG. 12 illustrates a plan view of yet another embodiment of the present invention, showing the graft on the intermediate body only;

FIG. 13 illustrates a plan view of yet another embodiment of the present invention, showing the graft at discrete positions on the body of the stent; and

DETAILED DESCRIPTION OF THE INVENTION

The following is a detailed description depicting some embodiments of the present invention. The description is meant to describe the intraluminal prosthesis embodiments, and is not meant to limit the invention in any way.

Figure 1:
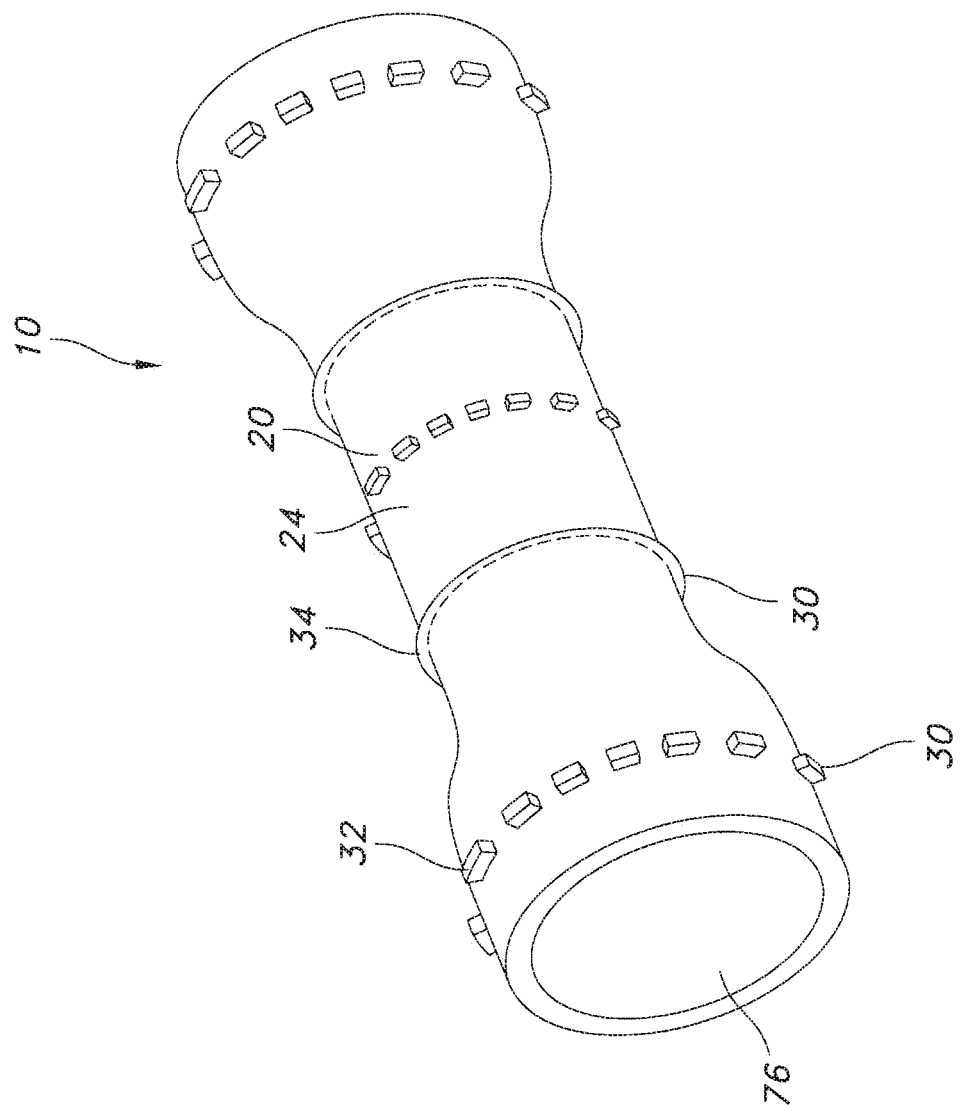
FIG. 1 illustrates a perspective view depicting an embodiment of an intraluminal prosthesis with 3D anti-migration structure formed thereon.
Figure 2:
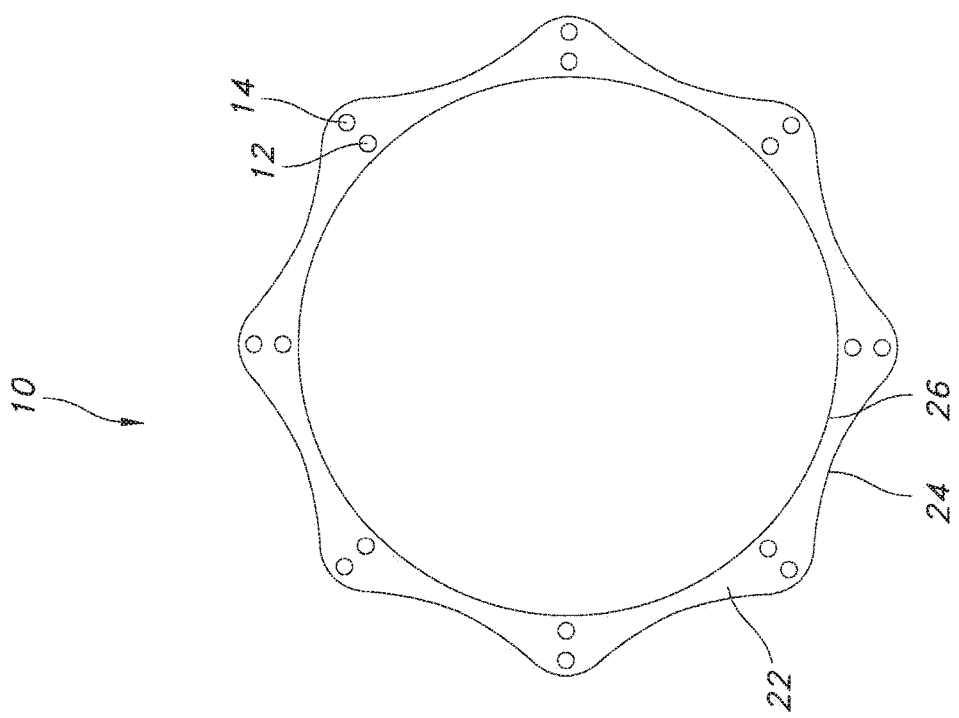
FIG. 2 illustrates a cross-sectional view depicting the stent of FIG. 1 along the line A-A.
Figure 4:
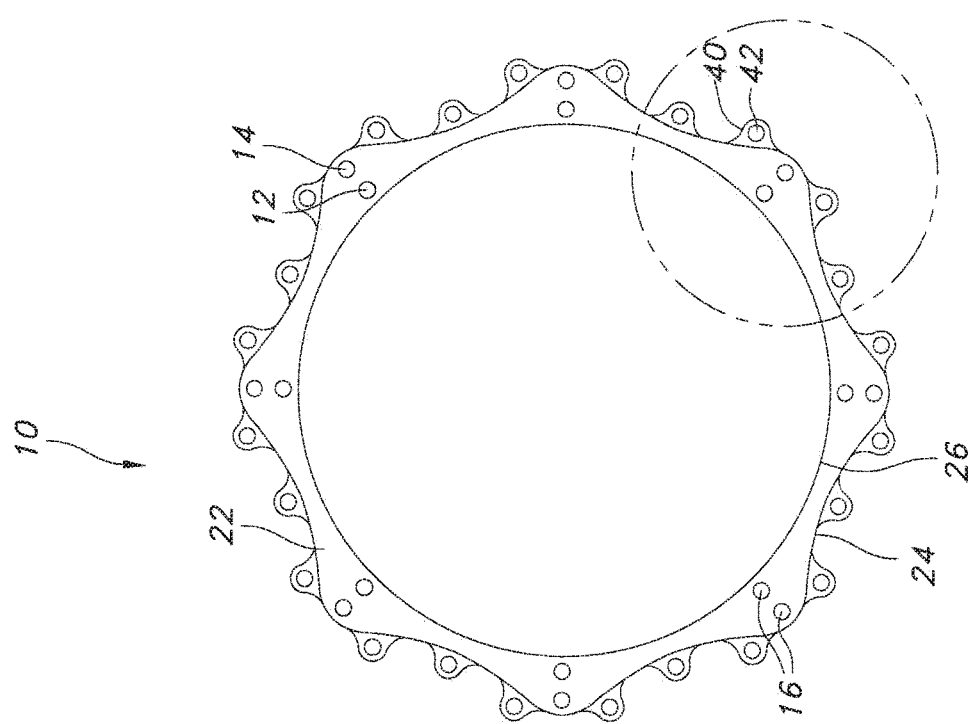
FIG. 4 illustrates a cross-sectional view of the stent along the line B-B of FIG. 3.
Figure 5:
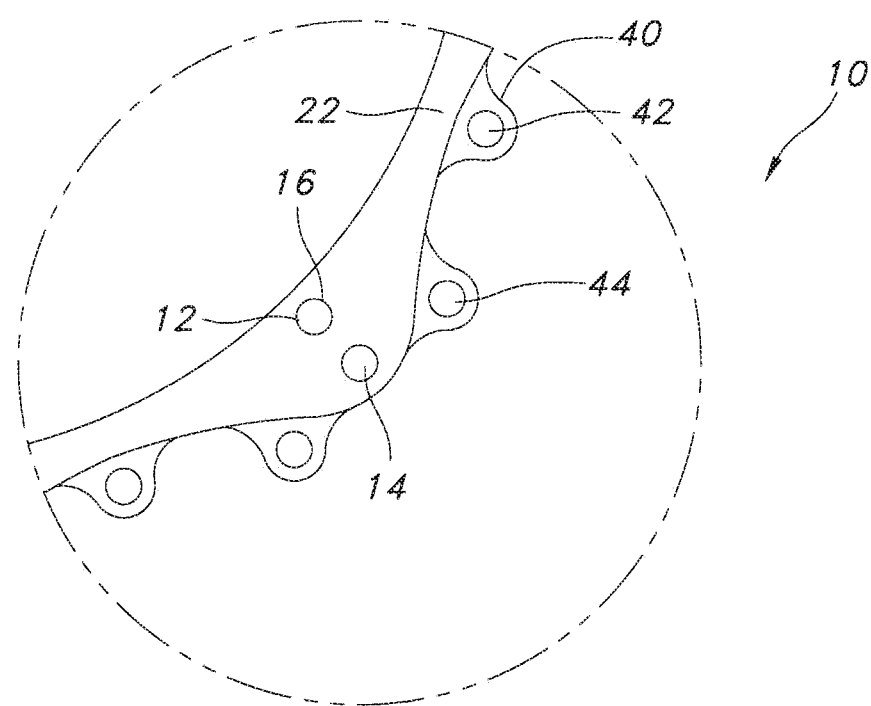
FIG. 5 illustrates a detailed view of the portion of the stent device encircled at "C" in FIG. 4.

FIGS. 1 and 2 depict different views of an intraluminal prosthesis 10. In one embodiment, the intraluminal prosthesis 10 includes a stent body 20 in a normal or relaxed configuration according to the present invention. The intraluminal prosthesis 10 can assume the normal or relaxed configuration when it is not subject to any external load or stress. As depicted in the cross-sectional view of FIGS. 2 and 4, the stent body 20 may be fully covered with an elastomeric membrane 22. The elastomeric membrane 22 is defined by an exterior surface 24 and an inner surface 26. Stent body 20 may include one or more wire stents 16. In one embodiment, the exterior surface 24 may at least partially cover a wire stent 16 (shown in FIGS. 6 and 7). Alternatively, inner surface 26 of the elastomeric membrane may cover the wire stent 16. As illustrated in FIGS. 4 and 5, wire stent 16 may include a pair of helically wound or braided metal or polymeric struts 12 and 14, which may be separate pieces or may be formed from one integral strand. Struts 12 and 14 may be any configuration desired, and may be braided, woven, knitted, twisted, conjoined, locked, or laser cut. Optionally, the struts 12 and 14 may include any other desired elements to form the wire stent 16.

Figure 6:
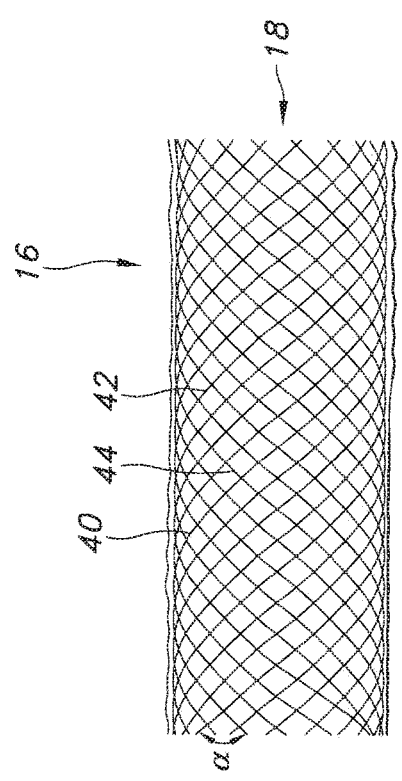
FIG. 6 illustrates a side plan view of another embodiment of the present invention with no flares at either ends and disclosing filament provided integrally with the stent struts directed at a particular direction having angle "α" with respect to an axis.

Referring back to FIGS. 3 and 4, stent body 20 includes several regions, including an intermediate region 32, a distal end cuff region 34 and a proximal end cuff region 35. The distal end cuff region 34 and the proximal end cuff region 35 may be shaped so as to have a wider cross-section than intermediate region 32, for example, which may be useful as an esophageal prosthetic device. Distal end cuff region 34 and proximal end cuff region 35 may include relatively wide flares 36, 37 disposed therein, which aid in forming the cross-section of the regions 34 and 35. In addition to its use as an esophageal prosthetic, the present invention may be used in any bodily vessel, such as in the coronary or peripheral vasculature, esophagus, trachea, bronchi, colon, biliary tract, urinary tract, prostate, brain, as well as in a variety of other applications in the body. These proximal and distal end flare regions 34, 35 of the present invention provide improved stent fixation, and thus, are particularly effective in resisting either proximal or distal migration of the stent body 20 itself. Flared cuffs 36, 37 may be designed with flexibility to readily conform to changes in the body lumen wall during the transmittal of bodily fluid or food. Alternatively, the present invention also envisions a stent body 20 having no flared end, or including one flared end as illustrated in FIG. 6. Stent body 20 may further include a medial sleeve disposed around the exterior of stent body 20, which may be disposed on any area of the stent body 20, including at least one of the intermediate region 32, distal end cuff region 34 and proximal end cuff region 35.

Generally, the exterior surface 24 of the intraluminal prosthesis 10 may be designed to be fairly smooth. If desired, a three-dimensional (3D) geometric structure 30 may be integrally formed with the elastomeric membrane 22. The 3D structure 30 may provide an anti-migration affect to the prosthesis 10. As depicted in FIG. 1, the 3D geometric structure 30 may be formed as a relief feature such as dots 32, beads (not shown), or rings 34. However, the 3D structure 30 may encompass any projection of figures or form shapes or other complex geometries which propel structural irregularity over the smooth exterior surface 24. When formed with the 3D structure 30 disposed over the smooth exterior surface 24, the stent body 20 is given an uneven contoured irregularity over the smooth surface 24, which may act as an added frictional point between the stent body 20 and the body lumen into which the stent body 20 is disposed. The added frictional interaction between the exterior surface 24 of the stent body 20 and the body lumen, facilitates anti-migration functionality, thus preventing or minimizing the movement of overall intraluminal prosthesis 10 in the body lumen. As will be appreciated by one of skill in the art, minimizing the movement of an intraluminal prosthesis 10 while in the body lumen is highly desired for both efficacy and safety reasons.

The 3D structure 30 may be configured to accommodate various tolerances in delivery systems which are to be used with the stent body 20. For instance, a stent body 20 is depicted in its relaxed or normal configuration in FIG. 3. As depicted, the intermediate region 32 may have a diameter of about 20 mm, and the cuff of the proximal region 34 and/or the cuff of the distal end region 35 may have a diameter of about 30 mm. In this particular embodiment, the struts 12, 14 forming the wire stent 16 may have a diameter of about 0.22 mm or less. The 3D structure 30 may preferably have a cross section of less than approximately 1 mm. This tolerance ensures that the overall diameter increase of the delivery device is kept, for instance, less than 2 mm (assuming one 3D structure 30 on opposed sides of the stent body 20). However, the present invention is not limited by the exemplary dimension tolerance. The total diameter may vary according to usage of the particular delivery device in a particular vessel. For instance, the dimensional tolerance for esophageal stent may be different from a coronary stent.

Figure 3:
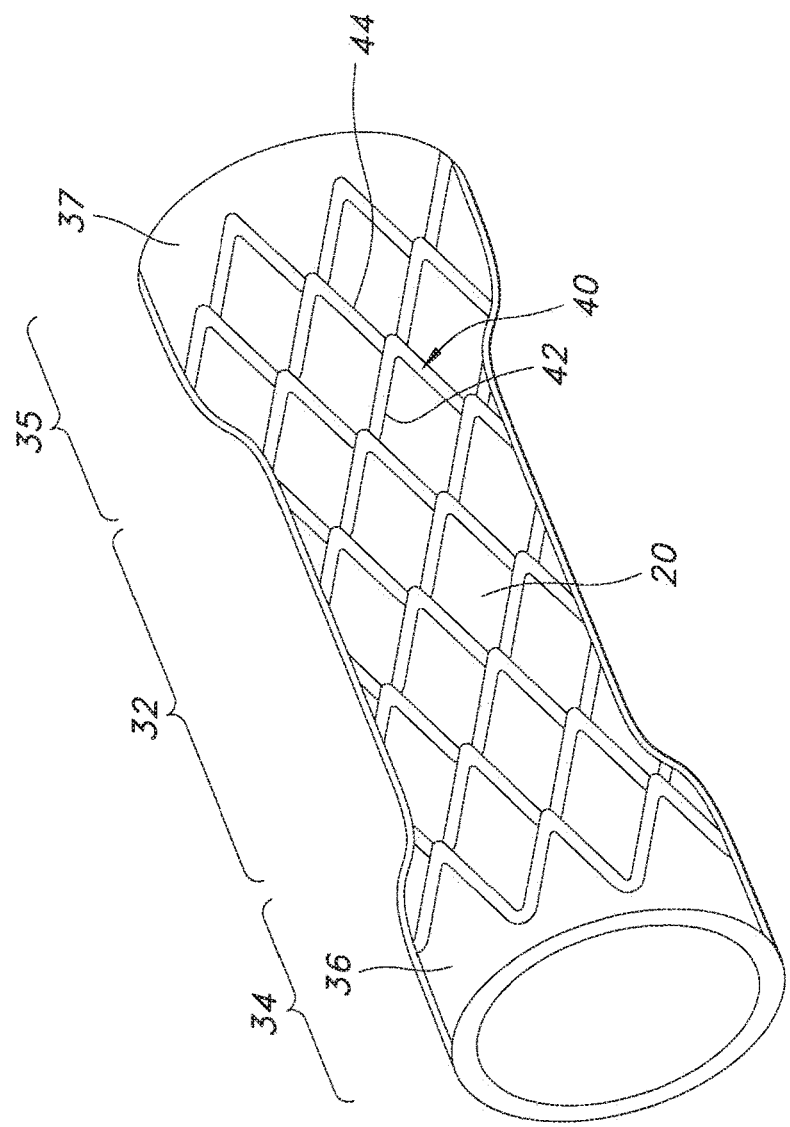
FIG. 3 illustrates a perspective view of an embodiment of a stent incorporating the anti-migration structure of the present invention, without depicting the visible struts for clarity.

FIG. 3 depicts yet another embodiment of the present invention in which the 3D structure 30 is not integrally formed with the elastomeric membrane 22. As depicted in FIG. 3, a thin discrete layer including strands of anti-migration filaments 40 may be disposed on the exterior surface 24. In one particular embodiment, the anti-migration structure layer 40 forms a pattern helically expanded about the exterior surface 24 of the intraluminal prosthesis 10. According to one embodiment of the invention, the anti-migration structure layer 40 may feature a plurality of individually rigid but elastically flexible anti-migration filaments 42, 44. Each filament 42, 44 may extend circumferentially in a helical configuration around the exterior surface 24. In some embodiments, the anti-migration filaments 42, 44 may span across a common longitudinal axis 18 of the stent body 20.

In another embodiment, the stent body 20 may be provided with the first set of filaments 42 having a common direction of winding but circumferentially displaced relative to each other. In this embodiment, the first set of filaments 42 may be configured to cross a second set of filaments 44 also circumferentially displaced relative to each other but winding in substantially opposite direction. In this embodiment, the stent body 20 is sufficiently configured to have anti-migration properties, as provided by the crossed filaments 42, 44. The directions of the filaments 42, 44 for the present invention are not limited by the above example, and also may extend lengthwise or perpendicular to the longitudinal axis 18. Further, the filaments 42, 44 may change direction at random locations, for example, they may be curved or wavy at random.

The device 10 of the present invention may encompass a 3D structure 30 configured to flex along certain selective dimensions. For instance, the 3D structure 30 may include an anti-migration structure layer 40, which may be flexible in a radially outward direction of the stent body 20. In addition, the anti-migration structure layer 40 may be rigid in the longitudinal direction 18. The radial flexibility of anti-migration structure layer 40 as well as the removable stent body 20 may allow the intraluminal prosthesis 10 to be easily compressed into a delivery device. Further, the rigidity of anti-migration structure layer 40 in the longitudinal direction 18 is useful to ensure anti-migration functionality once the stent body 20 is positioned within a body lumen. The anti-migration structure layer 40 may impart such abrasive/frictional force against the interior surface of a body lumen that it will resist its longitudinal migration within the body lumen.

Various methods of forming the intraluminal prosthesis 10 are provided herein. In one embodiment, during the fabrication process of the stent body 20, the anti-migration structure layer 40 may be added to the wire stent 16 after the outer surface 24 is disposed on the wire stent 16. In an alternate embodiment, the anti-migration structure layer 40 may be formed integrally with the wire stent 16. Instead of the anti-migration structure layer 40 completely wrapping over exterior surface 24, the filaments 42, 44 of the anti-migration structure layer 40 may be interwoven with the wire stent 16. In this embodiment, the filaments 42, 44 may be partially or wholly covered by the exterior surface 24.

In one embodiment, depicted in FIG. 5, the adherent anti-migration structure layer 40 may include filaments 42, 44 having smaller diameter than the diameter of the struts 12, 14. In an alternate embodiment, the filaments 42, 44 may have larger diameters than the struts 12, 14. Further, some filaments 42, 44 may have smaller diameters than some struts 12, 14, while other filaments 42, 44 may have a larger diameter than some struts 12, 14. The present invention encompasses filament and stent body diameter of all ranges related to their uses. For instance, in the exemplary esophageal application, the anti-migration structure layer 40 may be formed with diameter less than 0.60 mm wide. Such dimension may ensure that it does not hinder the loading and removal of the stent body 20, while still remaining effective in its anti-migration functionality.

Figure 7:
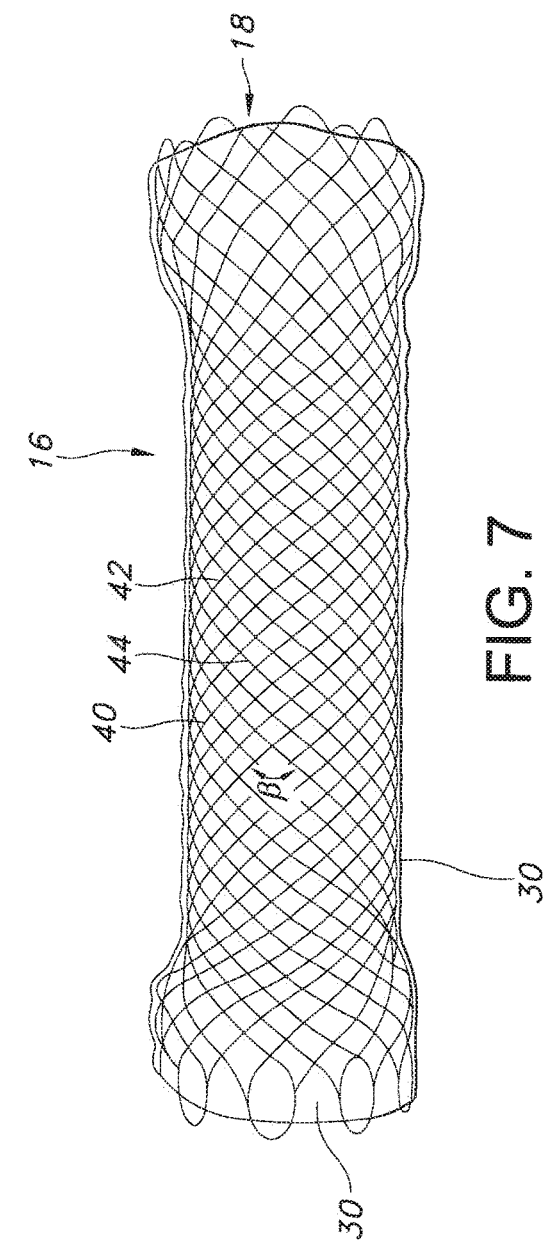
FIG. 7 illustrates a side plan view of the stent device as shown in FIG. 3, teaching the filament forming a second angle "β" with respect to the axis.

If desired, the anti-migration structure layer 40 may have a particular angle arrangement with respect to the longitudinal axis 18 of the device 10. As illustrated in FIG. 6 of the drawings, the filaments 42, 44 of the anti-migration structure layer 40 may be helically wrapped or arranged around the stent body 20 at a first angle alpha ($\alpha$). The angle $\alpha$ may be selectively placed to be non-congruent to a second angle beta ($\beta$), as seen in FIG. 7. This pattern of construction may allow the prosthesis 10 to be thin-walled, compliant, and more flexible, as it provides structural integrity while using less covering in the form of the anti-migration structure layer 40. Alternatively, the filaments 42, 44 may be angled at a different angle $\beta$, which may provide a more perpendicular frictional force as compared to angle $\alpha$, between the anti-migration filament windings and longitudinal axis 18. Thus placed, the anti-migration structure layer 40 may allow enhanced securement of the stent body 20 to the body lumen using less material than previously used in prostheses of this type. Thus, a particular angular arrangement of the filaments 42, 44 of the anti-migration structure layer 40 may allow for a more flexible and thinner composite prosthesis compared to a wider angled structure layer. Both angles $\alpha$ and $\beta$ may equal any value ranging from 0° to 180° with respect to the longitudinal axis 18.

Yet another advantage of the anti-migration structure layer 40 being disposed on the elastomeric membrane 22 is that it may provide structural reinforcement along the stent body 20. This reinforcement may enable the wire stent 16 to be constructed with a reduced angle of struts 12, 14. As used herein, the angles between the struts 12 and 14 is measured based on the strut incline deviation from the longitudinal axis 18 of the wire stent 16. FIGS. 6 and 7, in particular, illustrate a low angle $\alpha$ and a high angle $\beta$ for the struts 12, 14 and the filaments 42, 44, respectively. In each case, the wire stent 16 may be oriented with its axial length in the horizontal direction.

In prior art applications, an angle of 45° from the longitudinal axis 18 may have been considered a lower practical limit for the angle of a mesh or open weave wire stent 16. Employing the present invention, however, may enable a reduction of the braid angle to as low as 35 degrees from the longitudinal axis 18. The advantage of a lower angle for the struts 12, 14 resides in the fact that the angle may contribute to the ratio of stent axial shortening to its radial increase structure. As the stent expands, either through use of self-expanding materials or through the assistance of a balloon, a lower angle facilitates greater radial expansion of the stent body 20. With a reduced braid angle, upon expansion, there may be less axial shortening for a given radial expansion. Due to the reduced axial "drift", the stent body 20 may be more accurately positioned within the body lumens during its deployment. Thus, the profile of an anti-migration structure layer 40 or an adhesive layer 48, in combination with the stent 16, may resist the extraneous stretching and assist in the precise positioning of the composite intraluminal prosthesis 10 inside a body lumen.

Various other parameters of the structures of the anti-migration structure layer 40 may be altered to control the migration of the stent in a body lumen. For instance, the orientation of the filaments 42, 44 may be positioned in a direction that approximates a substantially perpendicular direction in relation to the longitudinal axis 18. The substantially perpendicular orientation of the filaments 42, 44 may further maximize migration resistance. The configuration and compositional makeup of the filaments 42, 44, the manner in which the filaments 42, 44 are attached, as well as the thickness of the filaments 42, 44 are some migration controlling parameters which shall be discussed below.

Referring now to FIGS. 7 through 13, several embodiments of the anti-migration structure layer 40 are shown, with the elements of the anti-migration structure layer 40 placed in various different pattern arrangements with respect to the removable stent body 20. Note that the orientation and configuration of anti-migration structure layer 40 may be varied to resist migration of the stent body 20 within the body lumen. The anti-migration structure layer 40 may have a diameter that is less than the diameter of the stent body 20, or may have a diameter that is greater than the diameter of the stent body 20. FIG. 7 depicts a fully covered stent body 20, wherein the stent body 20 is substantially fully covered with an anti-migration structure layer 40. In such embodiment, a braided anti-migration structure 40 could be made so as to match the strut braiding angle and expand/compress in concert with the struts 12, 14. As described above, the anti-migration structure layer 40 may be formed on the stent body 20 itself prior to applying an elastomeric membrane 24. Such composite anti-migration stent structure may be formed at the same angle and at same phase with each other. Alternatively, the anti-migration filaments 42, 44 may be at a different phase from the struts 12, 14. Further, the number of filaments 42, 44 in relation to the stent struts 12, 14 may be varied, as desired by the user. The filaments 42, 44 of the anti-migration structure layer 40 may wind at more than one angle with respect to the longitudinal axis 18. The bisecting pattern of strand filaments 42 and 44 depict different orientation (as well as the different angles) with respect to longitudinal axis 18. When each filament 42, 44 may intersect the other filament 42, 44, the intersection where the strand filaments 42, 44 bisect each other may be defined as nodes 49. These nodes 49 may form the adhesive positions for the filaments 42, 44. In another embodiment, filaments 42, 44 may be sintered to themselves at the segment where they intersect at node 49, as well as to the tubular prosthesis body 20 itself. Any means to secure the filaments 42, 44 to the intraluminal prosthesis 10 may be used, and may include the use of adhesives or sintering as desired.

FIG. 8 depicts yet another embodiment of the present invention, which is configured with a knitted anti-migration pattern on a stent body 20 of prosthesis 10. The anti-migration structure layer 40 may form loops at wave-like peaks 45 in order to secure the anti-migration layer 40 to the outer surface 24. The windings may be arranged on the nested stent body 20 in such a manner that upper wave-like peaks 45 may be nested within successive lower wave-like peaks 47 of adjacent windings. This knitting configuration may provide for subsequent anti-migration filaments 42, 44 on preceding structures where the preceding peaks 47 may intersect the subsequent peaks 45 to form elbow loops of coincidence or eyelet nodes of nodes 49. One of the main advantages of a knitted structure is that its orientation may be configured in a direction substantially perpendicular to the direction of the longitudinal axis 18. This pattern may provide greater frictional resistance to migration within the body lumens.

FIG. 9 illustrates an anti-migration structure layer 40 secured around the stent body 20 in a spiral fashion. The spiral pattern of the anti-migration structure layer 40 defines a plurality of spaced apart windings 51. Spaced apart windings 51 are disposed at a first angle with respect to the longitudinal axis 18 of the stent body 20. Successive windings 51 are positioned at a particular angle (as depicted with directional arrow 53) theta "γ" with respect to the longitudinal axis 18. As can be noted in the Figures, spiral winding 51 may be patterned in a straight line or in a wavy pattern analogous to a moire design. A wavy pattern may provide additional structural irregularity over the exterior surface 24.

FIG. 10 depicts a loosely woven anti-migration structure layer 40, which is repeatedly wound as both ring filament winding 57, 59 and longitudinal filament winding 55 substantially parallel with respect to the longitudinal axis 18 in a checker-board pattern. As depicted, the anti-migration filament 55 may be wound along the axis 18 and around the circumference of the stent body 20. FIG. 10 also depicts parallel windings of the filament 57 in such a manner that each upper winding 57 and lower winding 59 of adjacent windings are parallel across the stent body 20. When the windings 55, 57, 59 of the anti-migration structure layer 40 are orientated in two different directions substantially perpendicular to each other and with respect to the longitudinal axis 18 as depicted in FIG. 10, the anti-migration features may minimize not only the lateral migration but also prevent rotational migration as well. The anti-migration filament 57 may intersect other filament 55 to form nodes of intersection 61. The anti-migration structure layer 40 may be adhered to itself at nodes 61, or may be adhered to itself, as well as to the exterior surface 24 of the prosthetic device 10. Preferably, the anti-migration structure layer 40 may be sintered to itself at the segment it intersects, as well as to the tubular prosthesis at nodes 61, but other means for attachment, such as adhesives, are contemplated.

FIG. 11 illustrates another alternative stent body 20 where the anti-migration structure layer 40 is disposed primarily on the stent flares 36, 37. This configuration is particularly suited for esophageal placement, but may be used in any desired application. In this embodiment, the filaments 63 of the prosthesis 10 may be constructed to further strengthen the frictional force between the flare portions 36, 37 and the body lumen. Further, the strand filaments 63, may be of mesh or open weave construction, or they may comprise multiple braided and helically wound strands. As a person skilled in the art would immediately recognize, the present invention is not so limited by these Figures. The anti-migration structure layer 40 may have a first arrangement at one end and a second arrangement at the opposite end, or it may have the same arrangement at each end. Further, there may be an anti-migration structure layer 40 disposed at one end, and no anti-migration structure layer 40 disposed at the opposite end.

FIG. 12 illustrates a stent body 20 wherein the anti-migration structure layer 40 is applied only to the intermediate body 32. In this aspect of the invention, the anti-migration structure layer 40 may be applied selectively to the intermediate body 32 so as to limit or slow the expansion of the intermediate body 32. Because the end flare portions 36, 37 are free of the anti-migration layer 40 in this particular embodiment, these flare portions 36, 37 may be free to engage the lumen or blood vessel wall. One advantage of this construction is that the end portions may be positioned to engage relatively healthy tissue surrounding the site of the stenosis or structural defect, avoiding trauma to the weakened tissue.

FIG. 13 depicts a stent body 20 where the anti-migration structure layer 40 is applied at various locations 65 on the stent body 20. By having such a configuration, the distance between two threads can be controlled and optimized so that the outer surface is roughened to create controlled friction for anti-migration purpose.

It is important to note that, in general, the anti-migration structure layer 40 may be applied to a bare or partially covered stent body, as well as on top of a stent-graft (such as an ePTFE covered stent) combination. In addition, the anti-migration structure layer 40 may be applied to a self-expanding or a balloon expandable stent. Further, although the stent embodiments above have been exemplified with two flares 36, 37, the same invention can apply to stents with one or no flares as seen in FIG. 6. Further, although only two struts 12, 14 and two filaments 42, 44 have been identified in this description, it should be understood that any number of struts may be used to form the wire structure 16, and any number of filaments may be used to form the anti-migration structure layer 40. In addition, any of the stent body 20, elastomeric membrane 22, or the anti-migration structure layer 40, and combinations thereof, may be radiopaque.

In general, coating of the device 10 with an elastomeric membrane 22 is designed to enhance patency (state of being open). In addition, the tubular coating may resist tumor ingrowth. The thickness of the elastomeric membrane 22 may be in the range of 0.003-0.01 inches (0.075-0.25 mm). However, such elastomeric membrane 22 may also be up to a range of 0.001-0.1 inches. In some embodiments, the elastomeric membrane 22 may include a silicone film layer. The elastomeric membrane 22 may be disposed onto the outer surface of the stent body 20 by any desired means, including by placing the elastomeric membrane 22 onto the surface, by extruding the elastomeric membrane 22 onto the outer surface, or by dipping or spraying the elastomeric membrane 22 onto the outer surface. In the case of elastomeric membrane 22 formed by dipping, the thickness of the elastomeric membrane 22 may be controlled primarily by the number of dip coating applications. In particular, any number from one to about ten dip coatings (and preferably three to five dip coatings) of the stent body 20 may result in a thickness within a desired range. The elastomeric membrane 22 of the prosthesis 10 may also be formed of polytetrafluoroethylene (PTFE/ePTFE). Considered alone, the coating should provide an effective barrier to tissue ingrowth. In addition, the elastomeric membrane 22 may be elastic, and thus may radially expand like the remainder of stent body 20. Thus, silicone construction, in general, may be engineered to exert constant, gentle pressure to help adapt to normal luminal patency, for instance of esophageal peristalsis as its smooth inner surface helps facilitate passage of fluid. Optionally, the ends of the prosthesis 10 may also be reinforced by continuous polymeric film to help resist hyperplasia.

Desirably, any or all of the components of the intraluminal device 10, including but not limited to the elastomeric membrane 22, the struts 12, 14, the filaments 42, 44 or the material of the anti-migration structure layer 40 are made of a biocompatible material, including metals or polymeric materials. Any materials may be used in the forming of these elements. In one embodiment, the elastomeric membrane 22 preferably includes silicone, but other materials having elastomeric and biocompatible characteristics are also envisioned by the present invention. Further, the various struts 12, 14 that form the stent body 20 and/or the filaments 42, 44 that form the anti-migration structure 40 may include a monofilament or multi-filament structure. By way of example and not limiting the invention in any manner, other materials for any or all of the components of the device 10 may include polyurethane (PU), polyethylene (PE), polytetrafluoroethylene (PTFE), or expanded polytetrafluoroethylene (ePTFE). Textile or fabric constructions comprising of PTFE or ePTFE yarns, filament extrusions, or mesh may also be employed.

Similarly, the three-dimensional geometric structure 30 or the elastomeric membrane 22 may also be formed of any combined material among other choices inclusive of silicone, PU, PE or ePTFE. Also, the 3D structure could be made out of a material that is different from the material used to cover the stent. Furthermore, it may also be desirable to coat the stent body 20 with an additional thin layer of polymeric covering material to improve the adhesion of any 3D structures 30 or the anti-migration structure layer 40. In this embodiment, any 3D or anti-migration structure 30 may be disposed on the outer surface of the polymeric covering material along any length of the polymeric covering material. Further, the 3D structure 30 or anti-migration structure layer 40 may be disposed along any desired length of the prosthesis. In addition to the polytetrafluoroethylene (PTFE/ePTFE) as mentioned above, examples of suitable biocompatible polymers also include, and are not limited to, polyolefins such as high density polyethylene (HDPE) and polypropylene (PP), polyolefin copolymers and terpolymers, polyethylene terephthalate (PET), polyesters, polyamides, polyurethaneureas and polycarbonates, polyvinyl acetate, thermoplastic elastomers including polyether-polyester block copolymers, polyvinyl chloride, polystyrene, polyacrylate, polymethacrylate, polyacrylonitrile, polyacrylamide, silicone resins, combinations and copolymers thereof, and the like. Other useful coating materials include any suitable biocompatible coating. Non-limiting examples of suitable coatings include hydrophilic materials, hydrogels, and the like. Useful hydrophilic coating materials include, but are not limited to, alkylene glycols, alkoxy polyalkylene glycols such as methoxypolyethylene oxide, polyoxyalkylene glycols such as polyethylene oxide and its copolymers, polyethylene oxide/polypropylene oxide copolymers, polyalkylene oxide-modified polydimethylsiloxanes, polyphosphazenes, poly(2-ethyl-2-oxazoline), homopolymers and copolymers of (meth) acrylic acid, poly(acrylic acid), copolymers of maleic anhydride including copolymers of methylvinyl ether and maleic acid, pyrrolidones including poly(vinylpyrrolidone) and its derivatives, homopolymers and copolymers of vinyl pyrrolidone, poly(vinylsulfonic acid), acryl amides including poly(N-alkylacrylarnide), poly(vinyl alcohol), poly(ethyleneimine), poly(carboxylic acids), methyl cellulose, carboxymethylcellulose, hydroxypropyl cellulose, polyvinylsulfonic acid, water soluble nylons, heparin, dextran, modified dextran, hydroxylated chitin, chondroitin sulphate, lecithin, hyaluranon, combinations and copolymers thereof, and the like. Other non-limiting examples of suitable hydrogel coatings include hydroxyethylacrylates or hydroxyethyl(meth)acrylates; polyethylene maleic anhydride, combinations and copolymers thereof, and the like. Additional details of suitable coating materials and methods of coating medical devices with the same may be found in U.S. Pat. Nos. 6,447,835 and 6,890,348, assigned to the common assignee as the assignee of the present invention, the entire contents of which are incorporated herein by reference. Other useful synthetic biocompatible polymeric materials include, but are not limited to, polyesters, including polymethylacetates, naphthalane dicarboxylene derivatives, and silks. The polymeric materials may further include a metallic, a glass, ceramic or carbon constituent or fiber. Useful and nonlimiting examples of bioabsorbable or biodegradable polymeric materials include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly(phosphate ester) and the like. Some other materials which may be used as the filament include, but are not limited to Polyether ether ketone (PEEK), fluorinated ethylene propylene (FEP), and polyimide (PI), polybutylene terephthalate (PBT), polyurethane rubber (PUR), and silicone rubber. Tape, thread, ribbon, or other elongate members may also be used. According to one embodiment of the invention, at least one and preferably all extrusions is composed of one or more commercially available grades of polygluconate, polylactic acid-polyethylene oxide copolymers, modified cellulose, collagen, poly(hydroxybutyrate), polyanhydride, polyphosphoester, poly(amino acids), poly (alpha-hydroxy acid) or related copolymers materials. Further, the stent body 20 may include materials made from or derived from natural sources, such as, but not limited to collagen, elastin, glycosaminoglycan, fibronectin and laminin, keratin, alginate, combinations thereof and the like.

In addition to or in contrast to the polymeric materials set forth above, the stent body 20, inclusive of struts 12, 14, and/or the anti-migration structure layer 40, inclusive of the filaments 42, 44, may include improved external imaging properties under magnetic resonance imaging (MM) and/or ultrasonic visualization techniques. MM is produced by complex interactions of magnetic and radio frequency fields. Materials for enhancing MRI visibility include, but not be limited to, metal particles of gadolinium, iron, cobalt, nickel, dysprosium, dysprosium oxide, platinum, palladium, cobalt based alloys, iron based alloys, stainless steels, or other paramagnetic or ferromagnetic metals, gadolinium salts, gadolinium complexes, gadopentetate dimeglumine, compounds of copper, nickel, manganese, chromium, dysprosium and gadolinium. To enhance the visibility under ultrasonic visualization, the various components of the prosthetic device 10 may include ultrasound resonant material, such as but not limited to gold. Further, the stent body 20 and/or the anti-migration structure layer 40 may be made from polymeric materials which may also include radiopaque materials, such as metallic-based powders or ceramic-based powders, particulates or pastes which may be incorporated into the polymeric material. Metallic complexes useful as radiopaque materials are also contemplated. The stent body 20 and/or the anti-migration structure layer 40 may be selectively made radiopaque at desired areas along the stent or made be fully radiopaque, depending on the desired end-product and application.

Further, portions of the stent body 20 and/or the anti-migration structure layer 40, for example stent struts 12, 14 and filaments 42, 44, respectively, may have an inner core of iridium or combination of thereof and an outer member or layer of Nitinol to provide a composite filament for improved radiopaqueness or visibility. For example, the radiopaque material may be blended with the polymer composition from which a polymeric wire is formed, and subsequently fashioned into the stent body 20 and/or the anti-migration structure layer 40 as described herein. Alternatively, the radiopaque material may be applied to the surface of the metal or polymer strut 12, 14 or filament 42, 44. In addition, any component of the device 10, including the 3D structure, or any additional elements beyond the stent body 20 and anti-migration structure layer 40 may include one or more radiopaque elements. Various radiopaque materials and their salts and derivatives may be used including, without limitation, bismuth, barium and its salts such as barium sulfate, tantalum, tungsten, gold, platinum and titanium, to name a few. Additional useful radiopaque materials may be found in U.S. Pat. No. 6,626,936, assigned to the common assignee as the assignee for the current invention, the entire content of which is incorporated herein by reference.

Further, the materials of the anti-migration structure layer 40 can be chosen to provide gradual and controlled expansion of the stent body 20 over time. Specifically, the expansion characteristics of the anti-migration structure layer 40 can be chosen to differ from the expansion characteristics of the wire stent 16. In addition, the construction of the anti-migration structure layer 40 and its configuration about the stent body 20 can be chosen in such a manner as to allow for partial expansion of the stent to an intermediate diameter; the construction may allow further expansion of the stent body 20 to transpire over a longer period of time to its fully self-expanding diameter. Such combination may be employed in combination with the individual filaments 42, 44 or variation of different threads which make up a strand suture or yarn, or multiple sutures, each having a different expansion rate. The materials providing expansion characteristics may be applied to the stent body 20 at any desired location, including the intermediate region 32, distal cuff region 34, proximal cuff region 35, and combinations thereof.

Although polymeric and other materials are envisioned, the anti-migration filaments 42, 44 may preferably be comprised of an elongate textile material. Use of textile fibers obviates the need to shape and mold a device into its ultimate working configuration. Many fibers have proven to be biocompatible with body tissues. The term "textile material" in this disclosure is meant to include any material which may be used to combine with other pieces of the same material to become part of a larger piece of fabric. Examples of such textile materials include Nylon and polyester. Polyester is commonly used because it is available in a wide range of linear densities and its low moisture absorption also gives good resistance to fast deterioration. Polyurethane is yet another polymer which may be, due to its elasticity.

Alternatively, the anti-migration structure layer 40 may be formed of a variety of other materials having similar properties as well. In order to comply with changes in stent dimensions between the compressed and expanded stent, the fibers may be elastomeric. Such an elastomer may comprise, for instance, LYCRA™ or a polyurethane fiber.

Graft material selection is not limited to those materials listed above, but may include others that are conducive to the biocompatibility, distensibility and microporosity requirements of endovascular applications. For example, biodegradable filament extrusions sold under the tradename MONOCRYL™ (Ethicon, Inc., Somerville, N.J.) may be used. Alternatively, although thread-like or suture structures have been specifically mentioned as examples, this invention contemplates the use of any material and configuration capable of serving as constraining elements. Synthetic biocompatible, biodegradable polymers, such as those which break down to substantially non-toxic compounds which are readily absorbed and/or eliminated by the body, may also be useful. The present invention is not limited to these materials for the monofilament or multifilament struts 12, 14 or filaments 42, 44. In addition, the monofilament or multifilament struts 12, 14 or filaments 42, 44 according to the present invention can be comprised of any materials and structures mentioned above including braided, twisted or other methods.

Any component of the prosthetic device 10, and particularly the anti-migration structure layer 40, may also include a therapeutic agent that may be released into the body over time. Useful therapeutic agents or drugs include but not limited to, anti-platelets, anti-thrombins, anti-tumor drugs, anti-hyperplasia agents, anti-plaque building agents, cytostatic agents, and anti-proliferative agents, or other drugs for a specific purpose. This may also include agents for gene therapy. The therapeutic agent or drug is preferably selected from the group of therapeutic agents or drugs consisting of urokinase, dextrophenylalanine proline arginine chloromethylketone (PPack), enoxaprin, angiopeptin, acetylsalicylic acid, paclitaxel, 5-fluorouracil, cisplatin, vinblastine, vincristine, sulfasalazine, mesalamine, sodium heparin, low molecular weight heparin, hirudin, prostacyclin and prostacyclin analogues, dextran, glycoprotein IIb/IIIa platelet membrane receptor antibody, recombinant hirudin, thrombin inhibitor, calcium channel blockers, colchicine, fibroblast growth factor antagonists, fish oil, omega 3-fatty acid, histamine antagonists, HMG-CoA reductase inhibitor, methotrexate, monoclonal antibodies, nitroprusside, phosphodiesterase inhibitors, prostaglandin inhibitor, seramin, serotonin blockers, steroids, thioprotease inhibitors, triazolopyrimidine and other PDGF antagonists, alpha-interferon and genetically engineered epithelial cells, and combinations thereof. The foregoing list of therapeutic agents is provided by way of example and is not meant to be limiting, as other therapeutic agents and drugs may be developed which are equally applicable for use with the present invention.

Other features, which may be included with any components of the intraluminal prosthesis 10 of the present invention include surface modification components, which may be used for ultrasound, cell growth or therapeutic agent delivery, varying stiffness of the stent or stent components, varying geometry, such as tapering, flaring, bifurcation and the like, varying material, varying wire cross-section, varying geometry of stent components, for example tapered stent filaments, varied cross-section, wire cross-section and the like.

The invention also encompasses various means of manufacturing the intraluminal prosthesis. As an example, and not limiting in anyway, the wire stent 16 of this intraluminal prosthesis 20 may be circumscribed, i.e. completely covered, with a continuous polymeric film, preferably silicone or polyurethane. The polymeric film may be applied to the wire stent 16 by any desired means, including by spraying or dip-coating methods. In one embodiment, the polymeric film may be applied by dip coating of wire stent 16, in which event the film initially covers at least one of the distal or proximal cuffs 34, 35. When a partially covered stent is desired, the polymeric film may be removed from that cuff prior to using the stent body 20.

Generally, when incorporated into the device 10, the 3D geometric structure 30 may also be integrally preformed with the elastomeric membrane 22. In another method, the 3D geometric structure 30 may be applied to the surface of the stent body 20 directly. In an alternate embodiment, the 3D structure 30 may be disposed on the membrane 22 after the membrane 22 has been disposed onto the stent body 20 by any means desired, such as by molding, attaching, or other methods known by a person skilled in the art. For instance, the 3D structure 30 can be machined, laser etched, sprayed or even molded on to the stent body 20 or the elastomeric membrane 22. In addition, the struts 12 and 14 may be constructed with contours, effectively fashioning the 3D structure 30 to the elastomeric membrane 22. If desired, the 3D structure 30 may be arranged in any desired pattern, such as a helical pattern, an open weave pattern, an open knit pattern, a molded pattern, and combinations thereof.

In another manufacturing method for the intraluminal prosthesis 10, the process involves continuous fiber winding. In this embodiment, a polymer melt, solution or dispersion is extruded through a small orifice to form a polymeric fiber on the surface of the stent body 20. The polymeric fiber can be arranged in a structured pattern or in random pattern similar to a non-woven structure such as Tyvek™. Alternatively, a structured pattern can be obtained by continuously winding the fiber onto a rotating mandrel, fiber binding taking place on the surface of the stent body 20 in a particular design as described above. Although this process may be especially useful with polymers that are good fiber formers, the present invention is not so limited. The covered stent body 20 may be additionally cured by heat/pressure to improve the binding process. Additionally, the adhesion between the the stent body 20 and the fiber. This may be accomplished, for instance, with a heat-shrink sleeve.

As a further illustration of the structure and the method described above, U.S. Pat. No. 4,798,606 assigned to Corvita describes a coiled monofilament polymer structure, and U.S. Pat. No. 6,056,993 to Anderson et al., assigned to Schneider, USA, describes several ways to produce a porous polymeric graft. The entire contents of U.S. Pat. Nos. 4,798,606 and 6,056,993 are incorporated herein by reference.

If desired for certain polymers, such as silicone, an electric field may be applied between the orifice and the stent body 20 to aid in a process, known as electrostatic spraying. In this technique, a polymer melt, solution or dispersion is extruded through a fine orifice and directed towards a rotating mandrel. The polymer is attracted to the mandrel by the applied voltage. The mandrel is then struck with a plurality of short polymeric fibers that eventually coat the mandrel.

In some cases, the short polymeric fibers may tend to coalesce, leading to a low porosity. This coalescence may be overcome by spinning at least one water insoluble fibrous component together with at least one separate water soluble fibrous component. The water soluble fibrous component may then be washed out leaving the desired porosity on the external surface. Of course, the present invention is not so limited by the above example of continuous fiber winding method. The present invention encompasses many variations of the winding method. For instance, several spinnerets may be used simultaneously on the mandrel to provide effective coating.

In another embodiment, a salt dilution method may be utilized to provide the 3D structure 30. In this method, a water insoluble resin is mixed with a water soluble salt. The salt resin combination is applied to the stent body 20, and then the salt may be rinsed out with hot water leaving a porous resin structure on which the 3D structure 30 is adhered.

FIG. 3 depicts the filaments 42, 44 of the anti-migration structure layer 40 which are disposed on the exterior surface of the stent body 20 along its substantial length. The term "adhered" as used in this disclosure refers to the attaching of one component (such as the anti-migration structure layer 40) to another component (such as the tubular stent body 20) in any desired manner. This term, "adhere" includes without limitation, lamination, thermally adhering, sintering, RF welding, attaching with an adhesive, and any combination of the above. Sintering, as used in the present disclosure means heating the composite prosthesis to a temperature below its melting point, yet sufficient to thermally adhere the prosthesis. The heat of sintering differs for different materials. An adhesive may be used in conjunction with the sintering process. Alternatively, the filament(s) may be adhered with an adhesive without sintering.

Other ways to attach the anti-migration structure layer 40 to the stent body 20 in lieu of the electrostatic method or the extrusion method are contemplated herein. For instance, such as that seen in FIG. 5, an adhesive layer 48 such as polymer like polyurethane may be applied to the exterior surface 24 of the stent body 20. The anti-migration filament structure layer 40 may be placed on top or below the adhesive layer 48. In some embodiments, the adhesive layer 48 can be sprayed or coated to the outer surface 24 and/or the stent body 20 at any desired locations. After the adhesive layer 48 is applied to the stent body 20, the anti-migration structure layer 40 and/or 3D structures 30 may be disposed over the adhesive layer 48. Preferably, the anti-migration structure layer 40 and/or 3D structures 30 are adhered to the stent body 20 with use of a combination of heat-shrink adhesive and heat. An alternative method is to place the anti-migration structure layer 40 directly on the stent body 20. After the anti-migration structure layer 40 is placed thereon, the stent body 20 together with the anti-migration structure layer 40 a polymer may be applied to the outer surface thereof. The polymer may be applied in any desired manner, including spraying, rolling, dipping, or the like. Any polymer may be used, and in one embodiment, the polymer includes polyurethane. The anti-migration structure layer 40 may be adhered non-continuously at selected areas, or may be adhered continuously throughout the entire length of the stent body 20. The present invention is not limited by above examples. For instance, a strip of melted polymer may be placed either underneath or on top of the anti-migration structure layer 40.

Preferably, the fabrication process can also minimize any openings or gaps in the prosthetic device 10, which may allow tissue ingrowth. Ingrowth may breed and develop on any opening or seam in the device 10. Such ingrowth may precipitate a gripping bond between the body lumen and the stent body 20, making it difficult to remove the stent body 20 after a period of time. The adhesion layer 48 of the present invention, possibly in combination with heating or sintering may help ensure that seams or openings are minimized or eliminated altogether.

A method of insertion and/or removal of the prosthetic device of the present invention is also provided. In one embodiment, the method may include various steps. First, a collapsed stent-graft prosthesis may be provided. The prosthesis may have any combination of shape, thickness, and position arrangement as desired, as explained above. The prosthesis is preferably disposed within a delivery device, such as a catheter or any other device. The delivery device may then be inserted into a selected region of a body lumen. For proper placement, markers may be used, including radiopaque markers and the like. Once properly positioned, the collapsed prosthesis may be released from the delivery device and expanded. To achieve expansion, the prosthesis may be self-expanding, or a balloon delivery system may be provided as is known in the art. The delivery device may then be removed. For various reasons, one may wish to remove the prosthesis after placement, in this fashion, a second delivery device may be inserted into the body lumen after placement of the prosthesis. This second delivery device preferably includes a grabbing mechanism. The user may then use the second delivery device to remove the prosthesis, desirably without removal of ingrowth generated on the prosthesis.

Although the present invention has been described with reference to embodiments, the above described embodiments of the invention are merely descriptive of its principles and are not to be considered limiting and those skilled in the art will recognize that changes can be made in form and detail without departing from the spirit and scope of the invention. For instance, although anti-migration structure layer 40 has been described for creating a friction surface, other types of structures such as non-woven coverings may be used instead of the three-dimensional (3D) structures 30 or threads to provide the rough surface. For instance, materials such as thin polymers, elastomers, plastic wires, or the metal wires of the stent itself are contemplated as being part of the invention. For instance, the 3D structures 30 can be combined with anti-migration filaments 42, 44 to provide a hybrid anti-migration structure. Accordingly, the particularly disclosed scope of the invention is set forth in the following claims.

What is claimed is:

1. An intraluminal prosthesis comprising:
    a radially expandable tubular stent structure having a circumference and a length defining a longitudinal axis, the expandable tubular stent structure having an interior surface, an exterior surface, and a plurality of openings extending through the tubular stent structure from the interior surface to the exterior surface, and wherein the tubular stent structure includes first and second flared end regions and a body region therebetween; and
    a polymeric covering surrounding the tubular stent structure and covering the plurality of openings, the polymeric covering having a first end, a second end and a length measured from the first end to the second end along the longitudinal axis;
    wherein the polymeric covering includes a plurality of projections extending radially outward from an outer surface of the polymeric covering, wherein an inner surface of the polymeric covering opposite each projection is devoid of projections or recesses along the entire length of the polymeric covering, wherein the plurality of projections include a plurality of polymeric annular rings integrally formed with the polymeric covering, wherein each annular ring extends continuously around the entire circumference of the expandable tubular stent structure, the plurality of projections configured to contact an inner surface of a body lumen to prevent migration of the prosthesis in the body lumen.

2. The intraluminal prosthesis of claim 1, wherein the plurality of projections further includes a plurality of beads spaced apart circumferentially around the tubular stent structure.

3. The intraluminal prosthesis of claim 1, further comprising an adhesive layer disposed between the polymeric covering and the exterior surface of the tubular stent structure to attach the polymeric covering to the expandable tubular stent structure.

4. The intraluminal prosthesis of claim 3, wherein the polymeric covering is non-continuously attached to the tubular stent structure with the adhesive layer at discrete areas.

5. The intraluminal prosthesis of claim 3, wherein the polymeric covering is continuously attached to the tubular stent structure with the adhesive layer throughout the entire length of the tubular stent structure.

6. The intraluminal prosthesis of claim 3, wherein the polymeric covering is a preformed covering attached to the tubular stent structure with the adhesive layer subsequent to formation of the polymeric covering.

7. An intraluminal prosthesis comprising:
a radially expandable tubular stent structure having a length defining a longitudinal axis, the expandable tubular stent structure having an interior surface, an exterior surface, and a plurality of openings extending through the tubular stent structure from the interior surface to the exterior surface, wherein the tubular stent structure includes a first flared end region and a body region; and
a polymeric covering surrounding the tubular stent structure and covering the plurality of openings, the polymeric covering having a first end, a second end and a length measured from the first end to the second end along the longitudinal axis;
wherein the polymeric covering includes a plurality of projections extending radially outward from an outer surface of the polymeric covering, wherein an inner surface of the polymeric covering opposite each projection is devoid of projections or recesses along the entire length of the polymeric covering, wherein the plurality of projections include a plurality of polymeric annular rings integrally formed with the polymeric covering, the plurality of projections configured to contact an inner surface of a body lumen to prevent migration of the prosthesis in the body lumen.

8. The intraluminal prosthesis of claim 7, wherein the plurality of projections are arranged circumferentially around the first flared end region.

9. The intraluminal prosthesis of claim 7, further comprising an adhesive layer disposed between the polymeric covering and the exterior surface of the tubular stent structure to attach the polymeric covering to the expandable tubular stent structure.

10. The intraluminal prosthesis of claim 9, wherein the polymeric covering is non-continuously attached to the tubular stent structure with the adhesive layer at discrete areas.

11. The intraluminal prosthesis of claim 9, wherein the polymeric covering is continuously attached to the tubular stent structure with the adhesive layer throughout the entire length of the tubular stent structure.

12. The intraluminal prosthesis of claim 9, wherein the polymeric covering is a preformed covering attached to the tubular stent structure with the adhesive layer subsequent to formation of the polymeric covering.

13. An intraluminal prosthesis comprising:
a radially expandable tubular stent structure having a first end, a second end, and a length extending therebetween, the expandable tubular stent structure having an interior surface, an exterior surface, and a plurality of openings extending through the tubular stent structure from the interior surface to the exterior surface, wherein the tubular stent structure includes a first flared end region at the first end; and
a polymeric covering surrounding the tubular stent structure and covering the plurality of openings, the polymeric covering having a first end at the first end of the tubular stent structure and a second end at the second end of the tubular stent structure such that the polymeric covering extends along the entire length of the tubular stent structure;
an adhesive layer disposed between the polymeric covering and the exterior surface of the tubular stent structure to attach the polymeric covering to the expandable tubular stent structure;
wherein the polymeric covering is a preformed covering attached to the tubular stent structure with the adhesive layer subsequent to formation of the polymeric covering;
wherein the polymeric covering includes a plurality of projections extending radially outward from an outer surface of the polymeric covering, wherein an inner surface of the polymeric covering opposite each projection is devoid of projections or recesses along the entire length of the tubular stent structure, the plurality of projections arranged circumferentially around the first flared end region, wherein the plurality of projections include a plurality of polymeric annular rings integrally formed with the polymeric covering, the plurality of projections integrally formed with the polymeric covering, the plurality of projections configured to contact an inner surface of a body lumen to prevent migration of the prosthesis in the body lumen.

14. The intraluminal prosthesis of claim 13, wherein the polymeric covering is non-continuously attached to the tubular stent structure with the adhesive layer at discrete areas.

15. The intraluminal prosthesis of claim 13, wherein the polymeric covering is continuously attached to the tubular stent structure with the adhesive layer throughout the entire length of the tubular stent structure.

16. The intraluminal prosthesis of claim 13, wherein the tubular stent structure includes a second flared end region at the second end, wherein the plurality of projections are arranged circumferentially around the first and second flared end regions.

17. The intraluminal prosthesis of claim 13, wherein the plurality of projections are a plurality of beads spaced apart circumferentially around the tubular stent structure.

* * * * *